(12) United States Patent
Soluri et al.

(10) Patent No.: US 6,232,605 B1
(45) Date of Patent: May 15, 2001

(54) FLAT SCINTILLATION GAMMA CAMERA, WITH VERY HIGH SPATIAL RESOLUTION, WITH MODULAR STRUCTURE

(75) Inventors: Alessandro Soluri; Roberto Pani, both of Rome (IT)

(73) Assignee: C.N.R. Consiglio Nazionale Delle Ricerche, Rome (IT)

( * ) Notice: Subject to any disclaimer, the term of this patent is extended or adjusted under 35 U.S.C. 154(b) by 0 days.

(21) Appl. No.: 09/202,790

(22) PCT Filed: Apr. 22, 1998

(86) PCT No.: PCT/IT98/00097

§ 371 Date: Dec. 22, 1998

§ 102(e) Date: Dec. 22, 1998

(87) PCT Pub. No.: WO98/50801

PCT Pub. Date: Nov. 12, 1998

(30) Foreign Application Priority Data

May 2, 1997 (IT) .............................................. RM97A0256

(51) Int. Cl.[7] .............................. G01T 1/208; G01T 1/00
(52) U.S. Cl. ...................... 250/366; 250/367; 250/363.02
(58) Field of Search .................................... 250/366, 367, 250/363.02

(56) References Cited

U.S. PATENT DOCUMENTS

| | | |
|---|---|---|
| 5,252,830 | 10/1993 | Weinberg . |
| 5,323,006 | 6/1994 | Thompson et al. . |
| 5,519,221 | 5/1996 | Weinberg . |
| 5,783,829 | * 7/1998 | Sealock et al. ...................... 250/367 |
| 5,864,141 | * 1/1999 | Majewski et al. .............. 250/363.02 |
| 6,021,341 | * 2/2000 | Scibilia et al. ...................... 600/407 |

FOREIGN PATENT DOCUMENTS 9637791   11/1996   (WO) .

* cited by examiner

*Primary Examiner*—Constantine Hannaher
*Assistant Examiner*—Otilia Gabor
(74) *Attorney, Agent, or Firm*—Browdy and Neimark

(57) ABSTRACT

The gamma camera, able to be developed in areas of any size and unlimited, presents such a thickness as to be considered flat and of minimal bulk and it can be assembled in individual modules to be attached one to the other solving the problem of dead zones between individual PSPMTS, with values of intrinsic spatial resolution in the order of 1 mm. The application of the present invention may range from the medical field (PET, SPECT, SPEM, PEM, etc.) to employment in astrophysics.

10 Claims, 11 Drawing Sheets

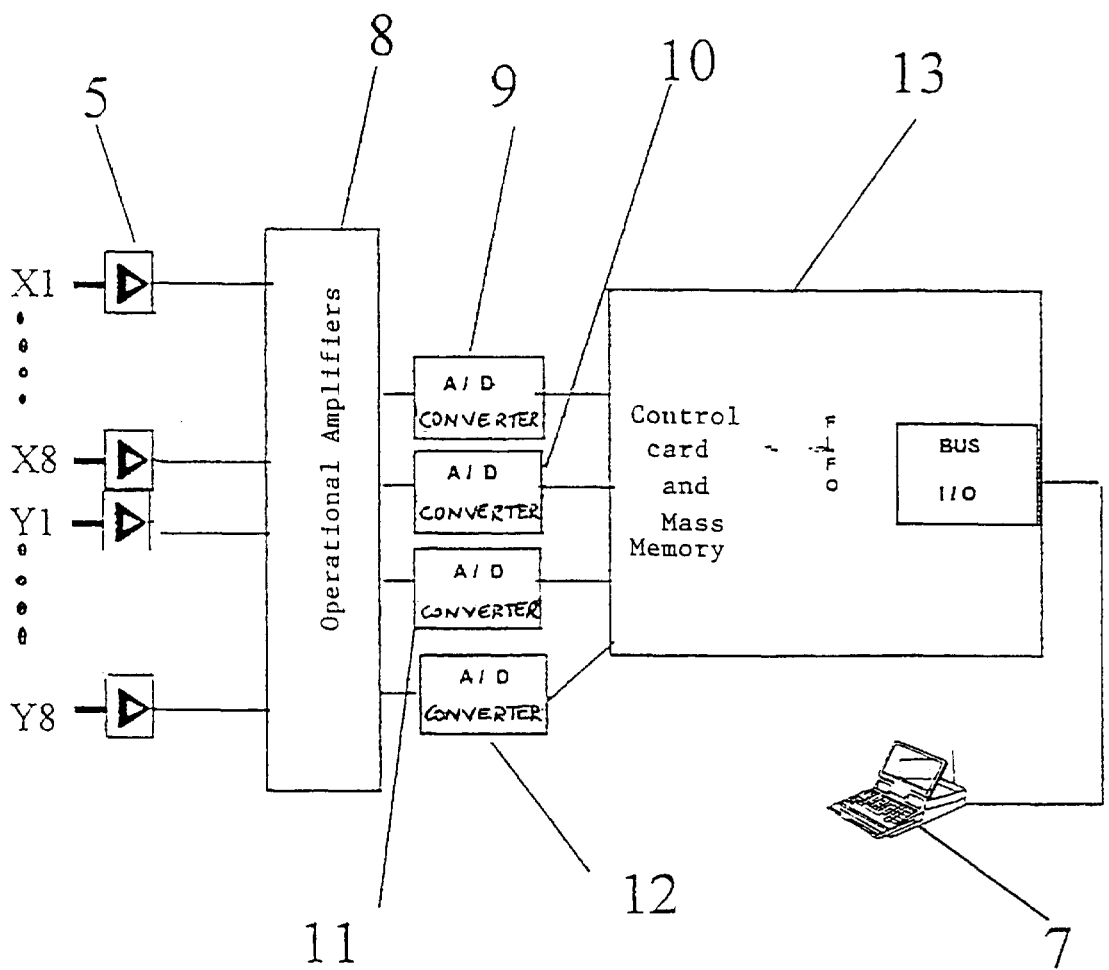
fig. 10
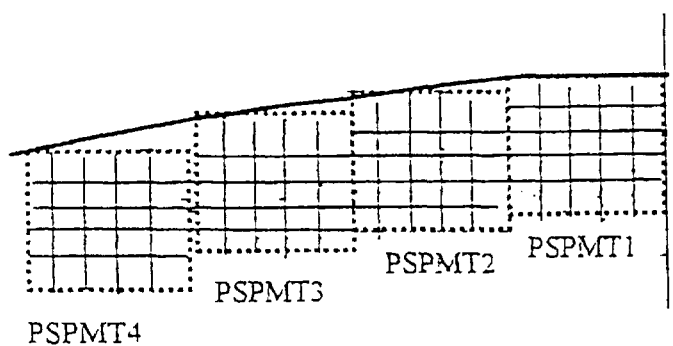

FLAT SCINTILLATION GAMMA CAMERA, WITH VERY HIGH SPATIAL RESOLUTION, WITH MODULAR STRUCTURE

The invention relates to a flat scintillation gamma camera, with high spatial resolution, able to be assembled in modular fashion, as it is composed of blocks which can be adapted to each other to form gamma cameras of variable sizes and shapes, from a minimum of 2 single blocks to an unlimited number, in such a way as to constitute the first flat scintillation gamma camera, unlike flat ones operating, with semi-conductor detectors.

Its application can find employment is all fields of oncological diagnostics in general and in some cases of radioimmuno guided surgery. It is well known that one of the most widely used devices for the localization of tumours is the gamma camera which uses tracers concentrating where receiving structures behaving as tumour formations exist.

In oncological diagnostics the use of the Anger Camera is quite widespread, although it does not reach satisfactory values of spatial resolution in the evaluation and prevention of tumours.

The principle of the Anger Camera consists of the use of a number of photo-multiplier tubes (PMTs in a number usually exceeding 30) coupled through a glass window to a single NaI planar crystal.

The gamma radiation, interacting in the scintillating crystal, generates a light distribution whose centroid coincides with the interaction point of the photon. The PMTs, reading from the different positions the portion of light quantity generated by the event, convert it into an electrical signal. An appropriate average, operated through a resistive-capacity network, allows one to obtain two signals for the position x and y. The main limitations of the Anger Camera consist of a spatial resolution of at least 3 mm, for the dimensions of the photo tubes having a diameter of about 60 mm and dead zone present between the PMTs in the order of 5–7 mm, the non homogeneous response of the photo cathodes, the light distribution which in this case must be broader than the diameter of the PMTs. Having fixed as technological limit for the scintillation performance that of NaI(Tl), under these conditions the limit value of spatial resolution cannot be better than 3 mm.

Another critical point is the peripheral dead zone.

Because of the broad distribution of light, an event close to the edge of the camera undergoes great deformations in position if it occurs at a distance of less than 5 cm; this entails a considerable limitation in the use of this camera for limited fields and imaging small organs and in particular anatomic adaptation applications.

Due to the Pb shielding necessary for the gamma ray detection connected to the use of passive Pb or W collimators, the thickness of the camera entails heavy weights (tens of kg) which limit its mechanical positioning use through special support and motion systems.

Moreover the broad distribution of light with circular symmetry limits preferred shapes to the circular one.

The active area of the current gamma cameras has progressively grown over time according to the technological capability of constructing ever larger scintillating crystals.

To improve the spatial resolution of the gamma camera based on Anger's principle, it is necessary to reduce the FWHM (Full Width Half Maximum) light distribution. Associated thereto, a reduction in the sampling size of the light (diameter of the PMT photo multiplier) results. This entails a quadratic increase of the photo tubes (5 mm of sampling entails a hundred-fold increase in the number of PMTs). Unfortunately, due to the technological difficulties related to the construction of photo tubes, the active area/dead area ratio decreases with the diameter of the PMTs entailing the loss of large fractions of light and large position uncertainties between individual PMTs. Moreover, the gain alignment procedures for hundreds of PMTs are particularly onerous and costly, in addition to the costs intrinsic in hundreds of individual PMTs.

The interest originated in the past few years towards the development of gamma cameras with high spatial resolution inevitably leads to hopes in a precocious diagnosis of tumours by means of ever more accurate and sophisticated technologies. Already the development of apparatuses dedicated to certain pathologies (such as SPEM=Single Photon Emission Mammography and PEM=Positron Emission Mammography dedicated to the assessment of breast carcinoma) moves the problem to the construction of machines dedicated to specific clinical applications. One of the needs of the new oncological diagnostics remains in any case linked to the possibility of having available versatile equipment, able to reach high spatial resolutions, at reduced costs. Already PET (Positron Emission Tomography) in some ways is wholly innovative for equipment dedicated to specific neurological pathologies.

The present invention constitutes a modular type of instrument, able to be adapted to different types of oncological investigations and, for the first time in the state of the art, able to adapt its constructive shape to the anatomy of the human body. This type of gamma camera in fact revolutionizes the concept of classic gamma camera like the Anger camera, further adding a technology able to attain extremely high levels of spatial resolution (in the order of 1–2 mm).

The modularity of the device stems from the use of individual Position Sensitive Photo-Multiplier Tubes (PSPMT), which behave as individual blocks to be joined without limitation, ranging from a minimum of two individual blocks to a variable number, thus attaining total areas of detection of any dimension.

The dimensions of each individual block are roughly 22 mm×22 mm or less of active area, and total size of about 30 mm×30 mm or less. The length of the individual photo tubes is about 30 mm, so that the thickness of the entire block can be defined as nearly flat with respect to a gamma camera which, on the contrary, has considerable bulk. The crucial technological problem is the one pertaining to the so-called "dead zones", i.e. the border zone between two photo tubes. Having solved this problem, using different technological solutions, individual blocks can be used to obtain different designs to be adapted to different requirements. The invention therefore constitutes the first scintillation gamma camera, of a flat type, to be used also according to differentiated sizes and at contained costs. In its simplest application variation it is possible to use just two blocks (about 3 cm×6 cm in area) for applications during surgical operations, or for external oncological diagnosis to detect small areas. An object of the invention, hence, is also the realization of an actual imaging system sensitive to gamma radiation, of variable dimensions, usable also for external diagnoses of turnouts of small dimensions (for instance skin melanomas, thyroid investigations, etc.). For instance, in order to remove a tumour surgically, the surgeon needs to localise it and, for that purpose, he/she normally uses the results obtained with the diagnostic systems employed to identify the tumour itself (radiography, CAT scans, NMR, Scintigraphy).

Such a technique can be replaced with the use of a standard gamma camera i.e. one having a single PSPMT which, although its dimensions are quite reduced, nonetheless still has considerable bulk during the surgical operation. Such information has a considerable advantage connected to the real-time display of any neoplastic formations and the confirmation of their total elimination after the surgical intervention for their removal.

Thus, the realisation is desirable of an actual imaging system sensitive to gamma radiations, of variable dimensions according to the different diagnostic needs, usable also for external diagnoses of tumours of small dimensions (for instance skin melanomas, thyroid examinations, etc.), since the reduced size, for example, can allow the total ease of handling of the device, with extremely reduced weight and the ability to visualize hard to reach areas of interest (between organs). Small detectors able to detect accumulations of radioactivity with spatial resolution of about 1 mm are thus applicable in this case. In the radioisotopic characterization of melanomas, and in general of skin tumours, the use of such high spatial resolution detectors is particularly useful: the suspected lesion is easily identifiable with a physical examination, so the detector can be positioned in the location of the suspected lesion and provide a reception map, with a response that can be roughly predicted as YES/NO.

The same line of reasoning applies to groin or armpit lymph nodes. The distinguishing feature of the present invention consists of the possibility to adapt shapes and sizes to the various diagnostic needs, using flat gamma cameras of small size, appropriately dimensioned, with obvious economic savings, without necessarily using traditional and/or large area gamma cameras.

Basic research on detectors tends to provide the nuclear physician with devices having ever improving spatial resolution, so as to detect radioactivity concentrations in small areas.

The modular device proposed herein comprises multiple Position Sensitive Photo Multiplier Tubes (PSPMT) coupled to scintillation crystals, a collimator of the same shape and area as the crystals and electronics suitable to process the signals from the photo tubes with processing software for real time visualisation of the areas of interest. Scintillation crystals, matrix or planar, can be of NaI (Tl), CsI(Tl), CsI(Na), YAP:Ce,BGO,GSO or other scintillation crystal.

Coupling the crystals with the photo tubes, through appropriate thicknesses of glass (quartz or materials with similar optical properties), allows to resolve the uncertainty of the dead areas, being able to provided information to retrieve those events which end up in the contact area between two contiguous photo tubes. The shape of the detector is suitable for any future evolution, not least the use of anatomic shapes for applications on the SPEM or PEM, in addition to affording the opportunity of constructing small gamma cameras of reduced cost, ease of transportation and modest weight. In particular, for mammoscintigraphic applications, the device enables to construct formats similar to the radiogram (for instance 15 cm×24 cm), easily allowing the fusion of the two diagnostic images. Moreover the limited dead zone of the present device allows to identify tumours near the thorax in the use in cranio-caudal projection, with or without breast compression. Lastly, also in cranio-caudal projection of the breast, the camera can be designed in such a way as to follow the profile of the attachment of the breast to the chest, up to the armpit attachment. This would allow for a better localization of any receptions of armpit lymph nodes and tumours near the attachment to the chest.

To attain this purpose, the invention has as its subject a flat gamma camera with very high spatial resolution, able to be used as external diagnostic device with the ability to detect tissue zones invaded by tumours of small area.

The object of the present invention is to solve the problems described above.

The object is attained with the present invention, which uses Position Sensitive PMTs allowing both light sampling at pitches equal to the collection anode of the camera (roughly 5 mm) and maintaining large the total area of detection of the PSPMT minimizing the dead area/active area ratio. According to the object, the invention is based on the use of cross wire anode PSPMTs, to be paired together as a single detection system, and the total dead area of two PSPMT is less than 6 mm.

It is essential to maintain the dead area/active area ratio as low as possible (and in any case less than 1) at the same time having a charge sampling (pitch between counterpoints of the anodes) of less than 1 cm to maintain high spatial resolution. For this requirement, the use of PSPMTs is optimal. In this case the distance between dead zone between two PSPMT active areas set side by side must be less than-equal to the sampling pitch. Another essential item for the present invention is the attainment of very high spatial resolution (approaching a millimetre) through a narrow distribution of the scintillation light subsequently converted into charge on the crossed wire anode, since this entails the reduction of the sampling pitch of the light.

The multi PSPMT gamma camera can have planar crystals in the thickness or matrices of scintillating crystals with light cone appropriately optimised according to the thickness of the glass window existing between photo tube and scintillation crystal, or alternatively coupling scintillation crystals and PSPMT photo multipliers with light guides. The light distribution in use shall not exceed 20 mm FWHM. Such value can be obtained by appropriately combining the thicknesses of the scintillating crystal with glass or quartz thicknesses to be paired with the photo tube. Alternatively, and by the same principle, it is possible to use matrix scintillation crystals of any size, in any case with area of the individual elements smaller than $3 \times 3$ mm$^2$, thickness variable according to the application and in any case no greater than 50 mm. In this case as well the scintillation crystals are to be combined with appropriate glass or quartz thicknesses to obtain a FWHM light distribution not exceeding 20 mm.

The reason why the gamma camera, according to the invention, can be defined flat consists of the use of PSPMTs of small area which afford the possibility of having reduced height, in any case smaller than 50 mm. In the case of use of planar crystals, the limitations are only linked to the technological ones pertaining to the use of large areas and thickness in order to obtain the characteristics indicated above. The use of crystal matrices does not limit the development of gamma cameras of large area. When assembling a series of PSPMTs, on the other hand, the problem remains of collecting the charge and determining the position of the event that generated the distribution of light on the photo multiplier tubes. Each PSPMT has a series of collecting wires to determine the X and Y position. The problem is to connect all collecting wires of all photo multiplier tubes, both for the X and for the Y position, so as to make such assembly of individual photo multiplier tubes appear as a single, unlimited anode collection surface. For this purpose the individual collection wires of each photo multiplier tube are connected with those of the next one and so on, until one has a single collection system connected to an electronic system able to provide the signals pertaining to the position of the X and Y co-ordinate. If for instance one wishes to connect four PSPMTs together, one can think of a matrix with two rows and two columns, wherein each element is an individual PSPMT. A photo multiplier tube has four wires for determining the X position and four wires for the Y position. The X position wires of the first PSPMT are connected with the analogous ones of the adjacent photo tube along the same direction (row) and so on. The Y position wires (column of the matrix) are connected in a wholly similar manner. The charge baricentre determines the position of the photon that hit the scintillation crystal. To attain this purpose, the invention has as its subject a flat gamma camera with very high spatial resolution, usable in different diagnostic modes, with application on small areas during surgical operations or for small organs, or as an external diagnostic device with the possibility of detecting tissue zones, as a traditional Anger camera.

The advantage of being able to define in an unlimited manner the dimensions of the camera and the additional advantage of being flat (thickness of a few centimetres), thus allows a technological advance.

Additional features and advantages of the invention shall be more readily apparent from the description that follows with reference to the accompanying drawings, provided purely by way of non limiting example, wherein:

FIG. 10 shows a block diagram of the electronics and of the output signals towards a personal computer.

With reference to the figures, the new gamma camera is shown, comprising:
- a collimator 1 made of Lead or high Z metal (such as W, Au, etc.) able to let through only the gamma radiations according to the solid angle crossing through its holes, and where the collimator has size equal to the area of the gamma camera;
- a scintillating crystal 2 made of CsI(Tl) with square matrix (with individual element of about 2 mm square and 3 mm thickness of Thallium-doped Cesium Iodide) sensitive to gamma radiations having energy ranging from a few keV to 1 MeV, with total size equal to a square with area equal to 60 mm×60 mm;
- a cladding 3 constituted by a coating of inert material with side of 65 mm and length ranging from 50 to 80 mm or more;
- a series of four PSPMT photo multipliers 4, able to collect the optical signals produced by the scintillation crystal and amplified into an electrical signal.

Figure 1:
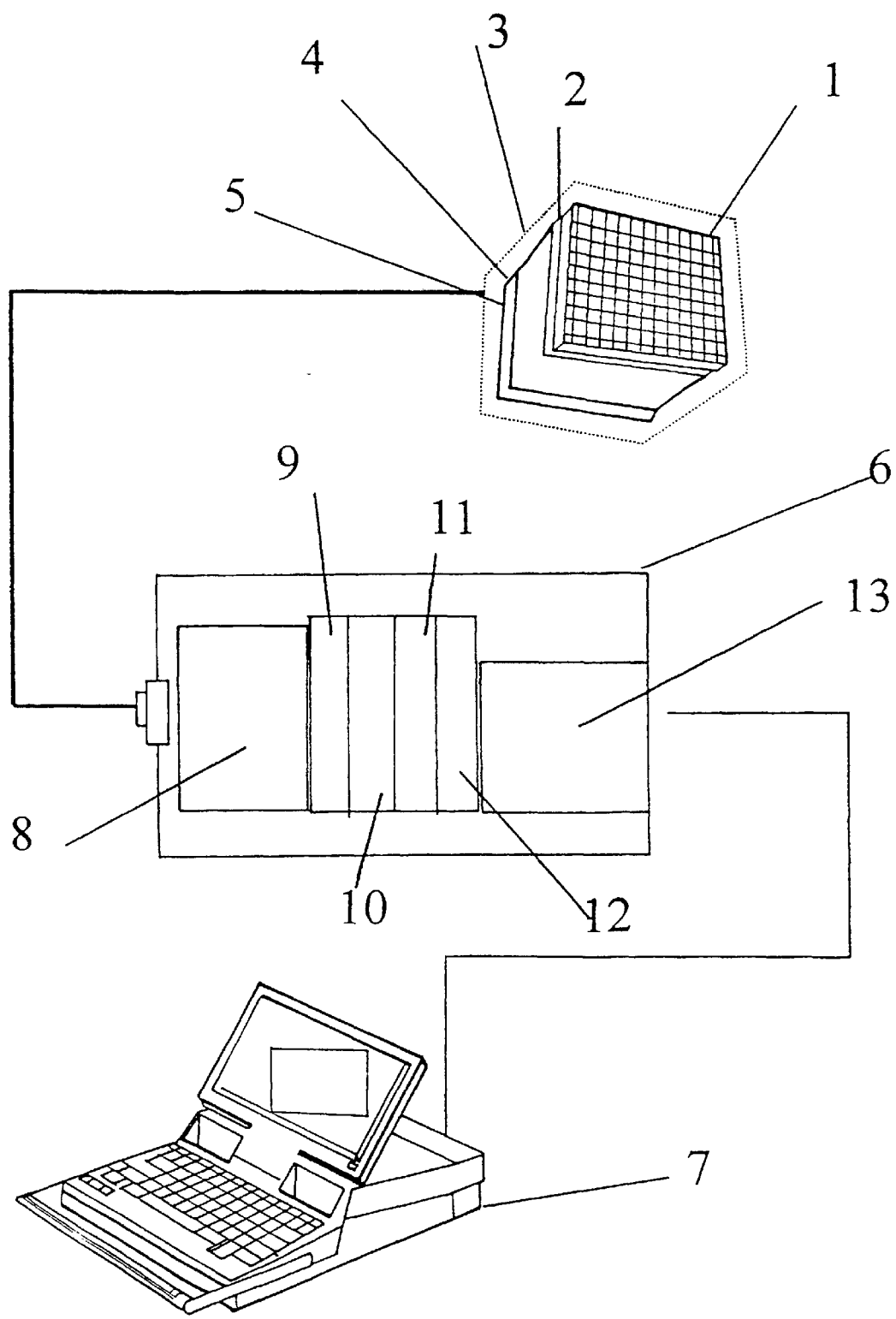
FIG. 1 is an enlarged scale view of the device wherein the parts comprising it are indicated.
Figure 2:
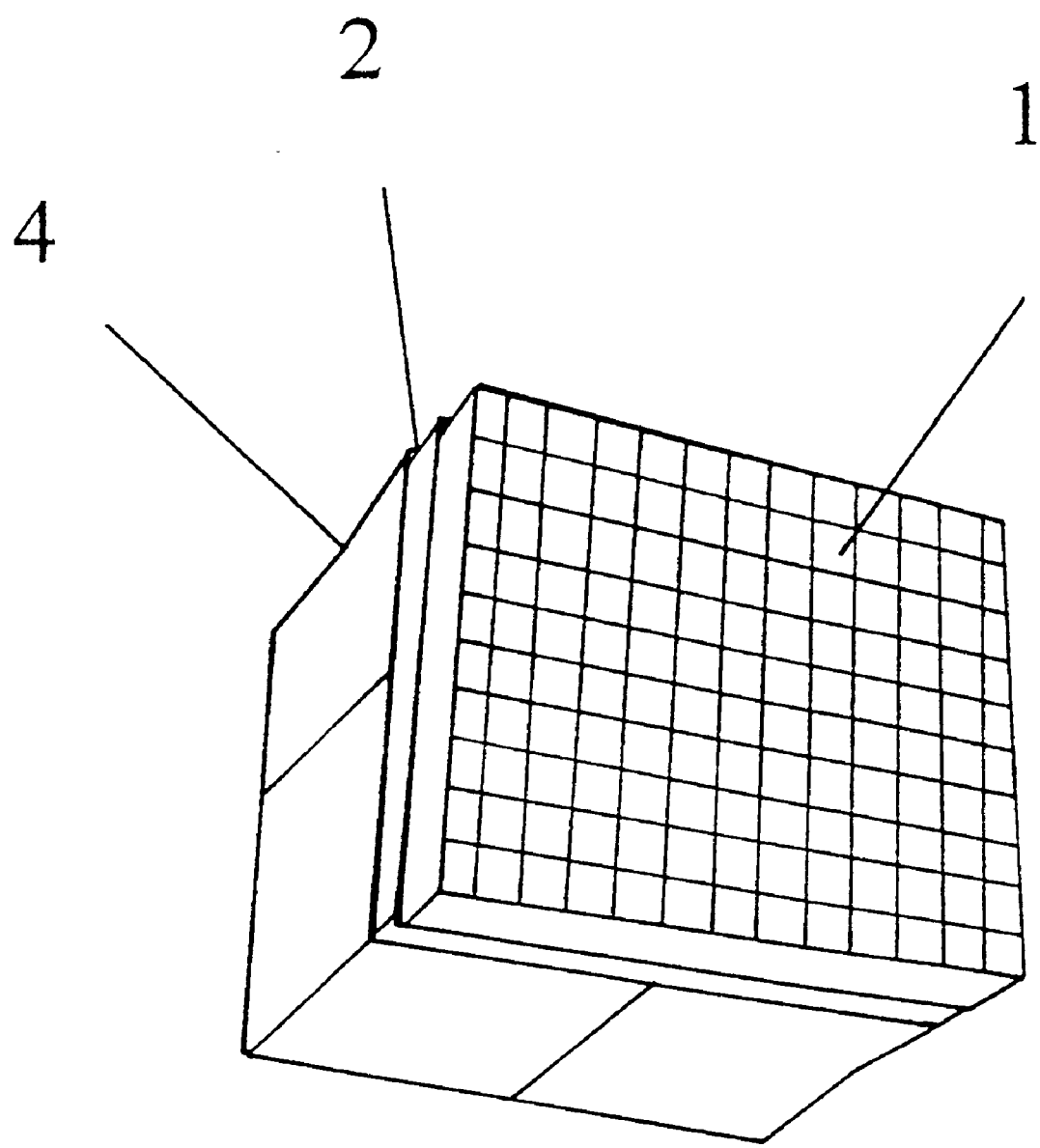
FIG. 2 shows the detail of the detection system formed by four paired PSPMTs.
Figure 3:
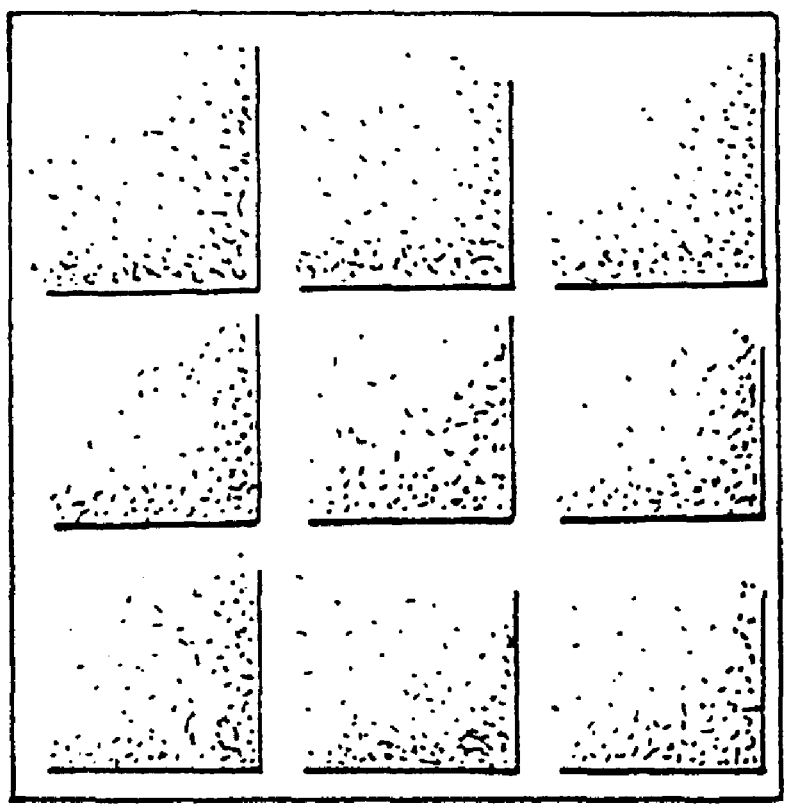
FIG. 3 shows the scintillating crystal matrix.
Figure 4:
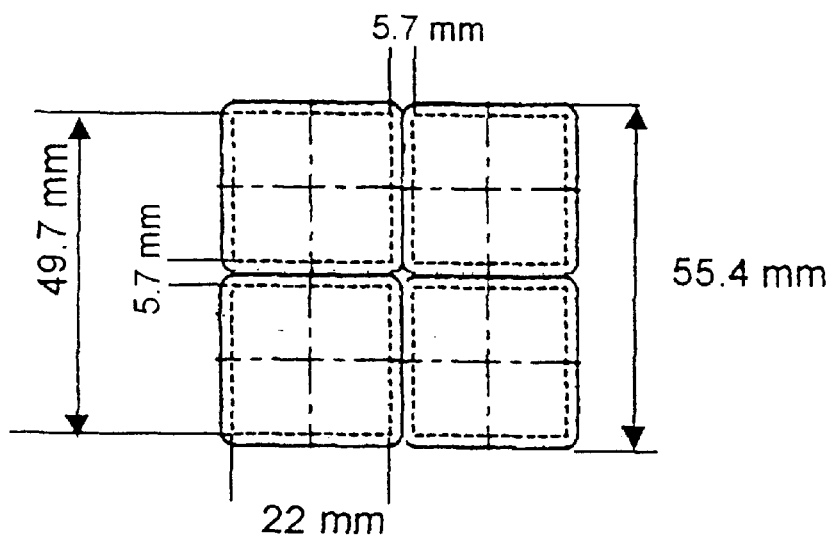
FIG. 4 shows a diagram of the coupling of a block of four PSPMTs and the related sizes of active area and dead zone.
Figure 4:
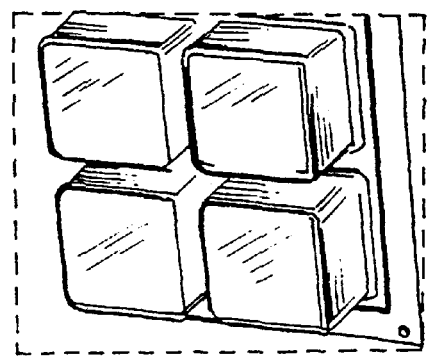
Figure 5:
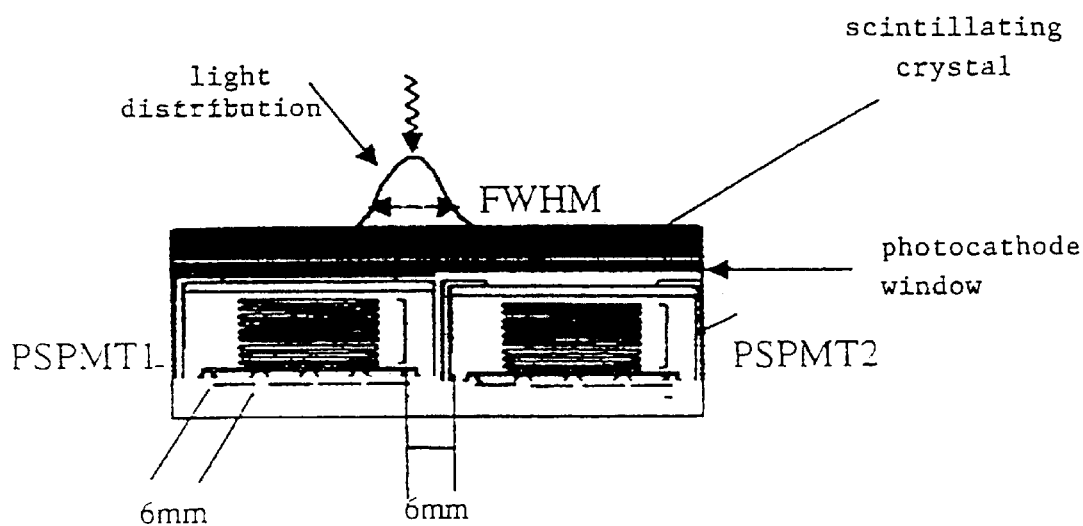
FIG. 5 shows the diagram of the charge distribution, in proximity to the dead zone between two PSPMTs.
Figure 6:
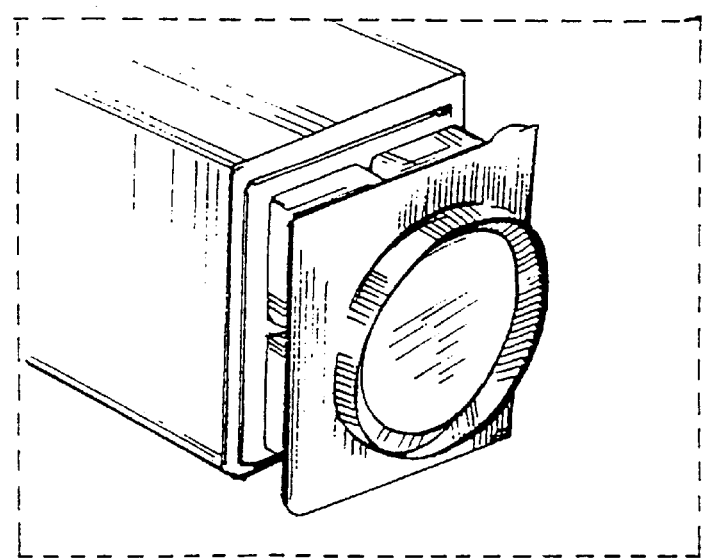
FIG. 6 shows an example of coupling between four PSPMTs and a planar crystal.
Figure 6A:
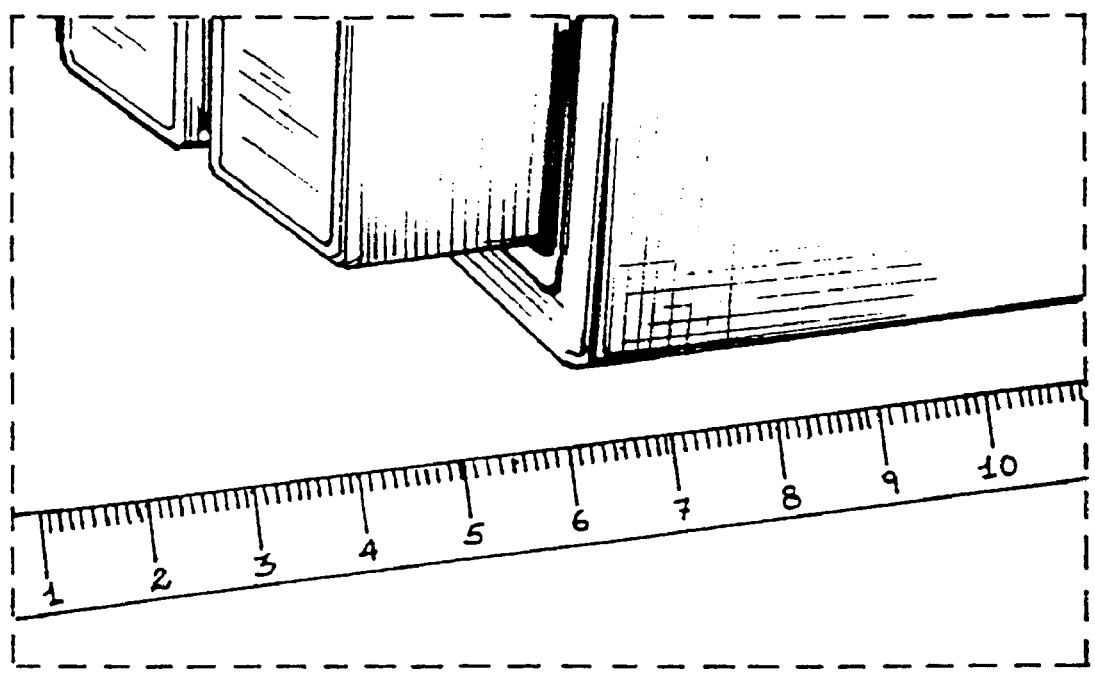
FIG. 6a shows a detail of the size of the detection header comprising the four PSPMTs and the related thickness.
Figure 7:
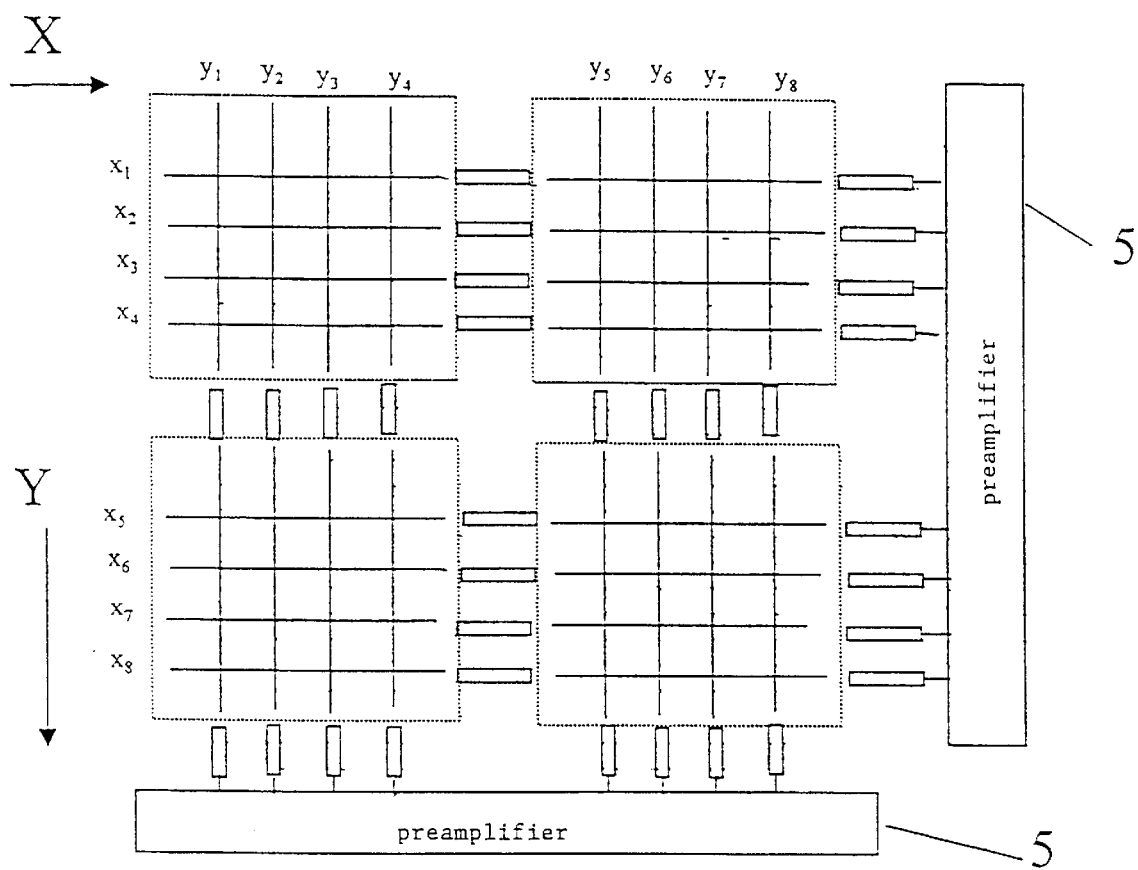
FIG. 7 shows the diagram of the connection between the anode wires exiting the individual PSPMT to each other and the related connection to the respective pre-amplifiers.

The photo multipliers used are of a compact type comprising thin metal channel dynodes encapsulated in a container having total height of about 30 mm and able to be position-sensitive with a multi-anode charge collection system. Subsequently, the eight signals exiting the individual photo multiplier tube (four for the X position and four for the Y position), are connected and continue with the corresponding elements of the contiguous photo multiplier tube, thereby forming a single collection area. In this way, as shown in FIG. 7, a total collection area will be obtained formed by eight wires along the X direction and four wires along the Y position; the signals exiting the connection of the PSPMTs are sent on eight pre-amplifiers 5 for the X position and eight pre-amplifiers for the Y position.

Figure 7A:
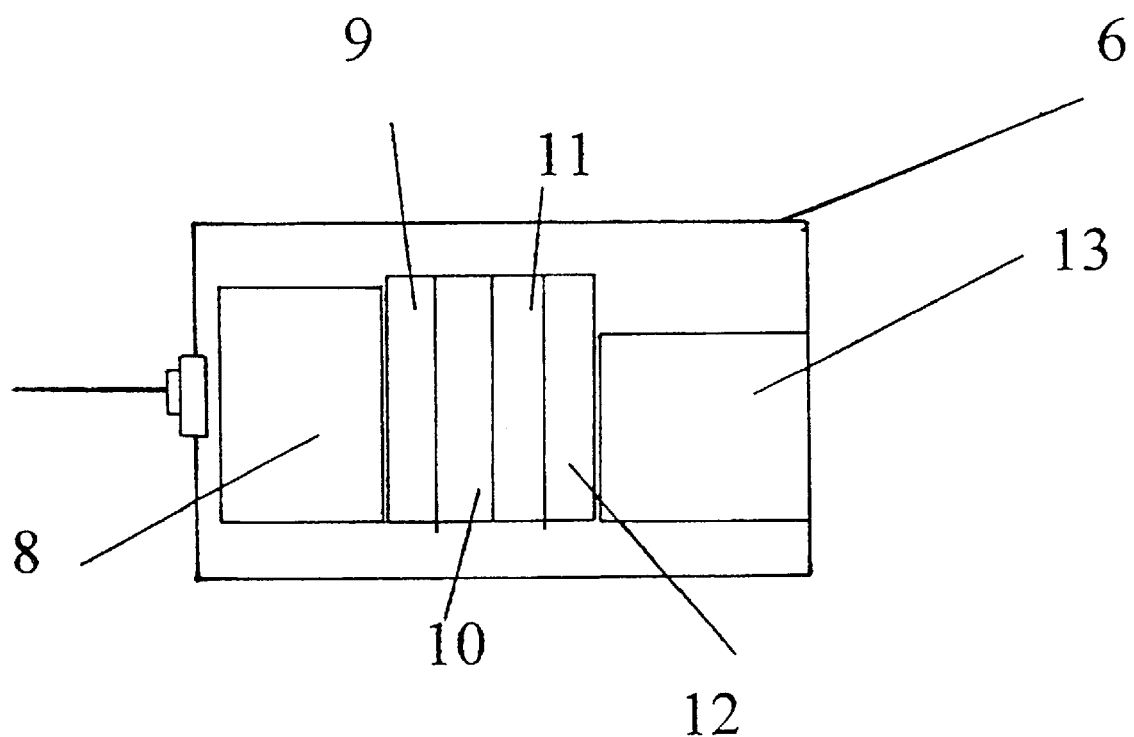
FIG. 7a shows the electronic block diagram required for operation.
Figure 8A:
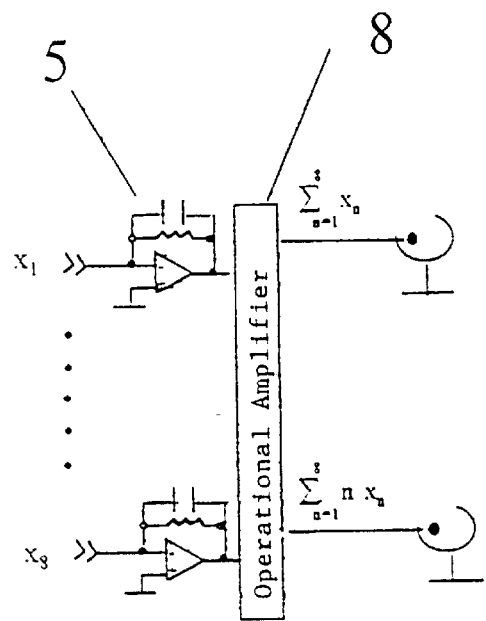
FIGS. 8a and 8b show the operating diagram of the operational amplifiers.
Figure 8B:
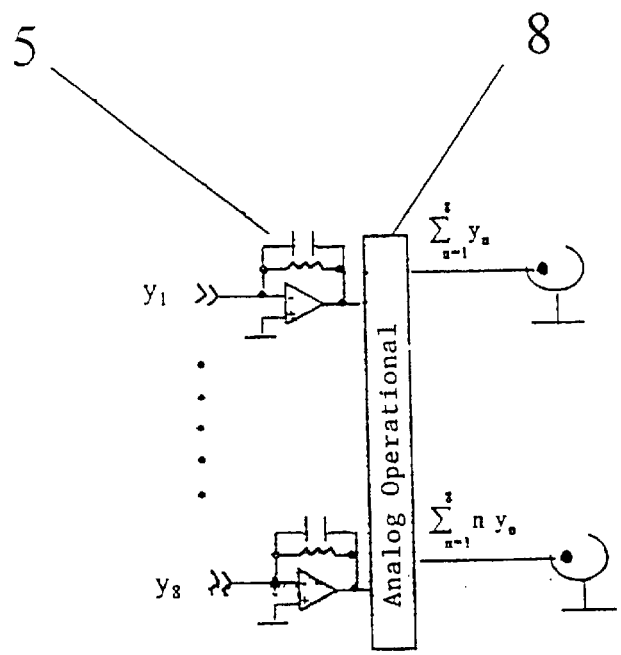
Figure 9:
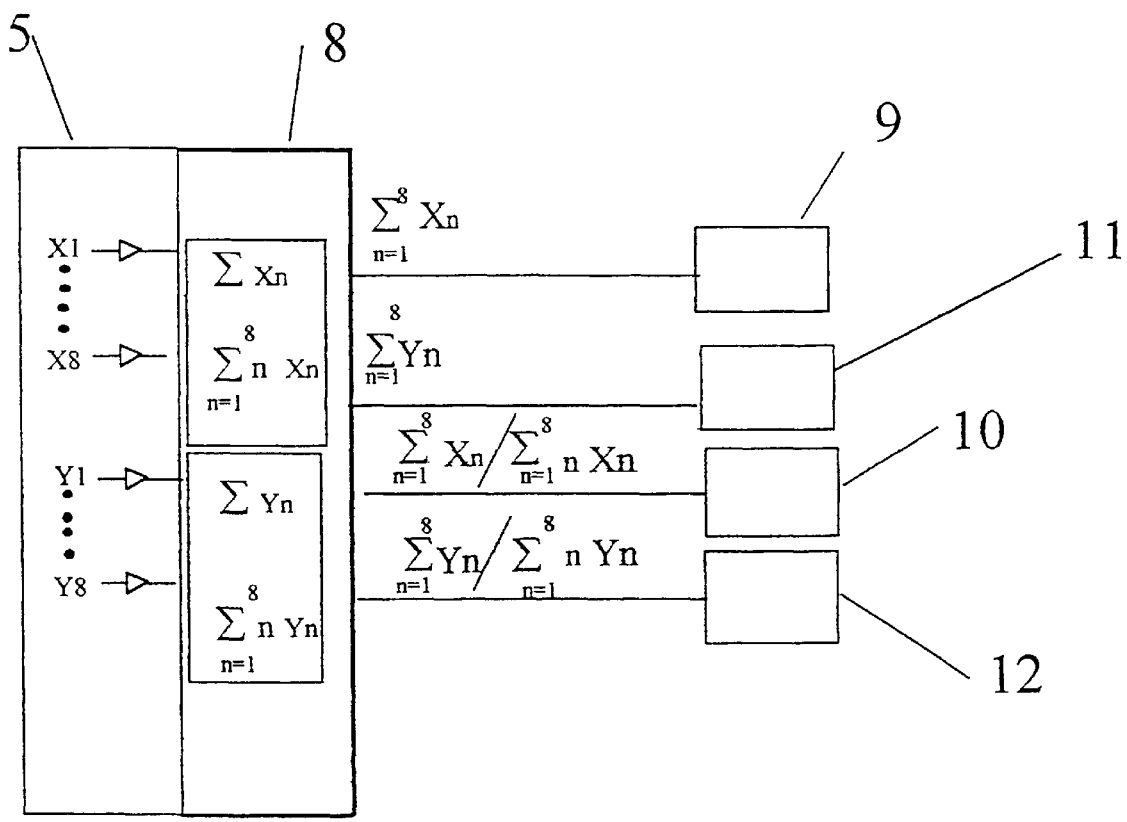
FIG. 9 shows a detail of the operating block diagram of the electronics for the conversion of the pulses from the amplifiers.

With reference to FIG. 7a a simplified set of electronics 6 is described which is used to obtain the sum of pulses exiting the pre-amplifiers and the subsequent digital conversion of the signals. The electronics comprise a block of operational amplifiers 8 and four converters 9, 10, 11 and 12 and a block 13 for transferring data to a personal computer 7. FIGS. 8a and 8b show a system of eight pre-amplifiers 5 for eight wire anodes for determining the position on the X axis and as many for the Y position. The electronic system for reading the charge collected on the anodes is accomplished by means of eight independent pre-amplifiers 5. Subsequently, the pulses are sent to a block of operational amplifiers 8 which perform hardware operations on the input signals With reference to FIG. 9 the processing mechanism of such signals is shown: from the operational block 8 exit four signals which subsequently enter four analogue-to-digital converters, whereof the converter 9 represents the value of the charge collected along the position X, the converter 10 represents the centroid for the X co-ordinate, and the converter 11 represents the value of the charge collected along the position Y. Such hardware calculation solution for the charge distribution centroid allows to minimize the data to be digitized and transmitted to the computer. With reference to FIG. 10, the output of the signals from the four converters is sent on a data acquisition control system 13, connected to a personal computer. The crucial point for data management is the transfer-rate to the computer which for cost reduction reasons shall take place using low-cost, standard computers, operating systems, and interfaces. Moreover, during acquisition the computer shall be able to present the image in "near" real time. In addition to having the capability of determining the position of the incident photon, it shall also be possible to determine its energy by summing the signal exiting the converter 9 (charge along X) and 11 (charge along Y), which contains the information of the charge released to the scintillation signal. In this way it will be possible to eliminate all those events caused by radiation scattering which are summed on the final image of the exam performed. With an appropriate energy window, it will be possible to correct the image complete with the "background", reducing the noise caused by single or multiple interactions in the body tissue, in such a way that the energy window shall discriminate only the photons of a given energy characteristic of the tracer used.

According to the invention, operational amplifiers 8 perform hardware operations on input signals for the computation of a charge barycenter to take place via weighted sum method, as represented by a formula for the barycenter. According to one embodiment, the operational amplifiers perform hardware operations on input signals having weighted resistance the collection of charge in position of the dead zone for computation of the charge barycenter.

The whole gamma camera is coated, with regard to cladding 3, with inert material.

A suitable presentation software is able to display the information as images of reception of the tracers injected into the patient, with the same representation typical of large-area gamma cameras.

The high sensitivity of the gamma camera, moreover, allows to use radio pharmaceuticals at different energies and it enables to mark specific antibodies for given tumours with different radio isotopes, commonly used in nuclear medicine.

In possible variations of the invention, the gamma camera can present, as scintillation crystal, a CsI(Tl) crystal matrix, where individual crystals have section of about 1 mm×1 mm and in any case ranging between 0.5 mm×0.5 mm and 3 mm×3 mm and where individual crystals are optically separated from each other, and the separation zone between crystal and crystal has thickness of about 0.1 mm and in any case ranging from 3 micron to 0.5 mm. Moreover, crystals of NaI(Tl), CsI(Na), BGO, LSO, YAP:Ce, etc., can also be used as scintillating crystals.

In an additional variation, individual PSPMT photo multipliers can be replaced with analogous ones having a greater number of dynodes and a higher number of charge collection anode wires, in order to reduce sampling pitch. As a consequence, the electronics are also modifiable by the same principle described above, in proportion to the number of outputs of the photo multiplier.

The dimensions of the photo multiplier used can also be varied, reaching larger dimensions but always in such a way that the dead area/active area ratio is smaller than 1. The principle of the invention is to obtain a device that makes use of position sensitive photo multiplier tubes, assembled in such a way as to constitute a gamma camera of unlimited shapes and dimensions and which at the same time is thin enough to be considered flat and which has a very high intrinsic spatial resolution.

In a possible variation of the invention, an assembly of PSPMT can be realised that follow a curvilinear anatomic profile. In this case the connection of the crossed anode wires shall not be of equal number for the calculation of the X and of the Y position. In this example the wire x1 of the first PSPMT is not connected to the analogous one of the subsequent PSPMT but rather is connected to the subsequent one and so on. The signals are offset by one anode pitch and in this situation the number of X wires is seven and the wires for the Y position are sixteen, so that the anatomic profile is obtainable according to the size of the anode pitch.

Obviously, moreover, the construction details and the embodiments may be varied widely with respect to what has been described and shown purely by way of example, without thereby departing from the scope of the present invention.

What is claimed is:

1. A flat scintillation gamma camera with very high spatial resolution, comprising a collimator (1), a scintillating crystal (2), a cladding (3), and a device able to collect optical signals produced by the scintillation crystal and amplified into electrical signals, wherein said device able to collect optical signals produced by the scintillation crystal and amplified into electrical signals comprises a plurality of square-shaped Position Sensitive Photo-Multiplier Tubes (PSPMT's) disposed adjacent one another, each PSPMT having a plurality of groups of collecting wires, with at least one group of collecting wires of each PSPMT being conductively connected to a group of collecting wires of an adjacent PSPMT, for calculation of X and Y positions; each said PSPMT having a side greater than 20 mm and a dead zone with a contiguous PSPMT smaller than 8 mm.

2. The flat scintillation gamma camera according to claim 1, wherein one said PSPMT has wires not connecting with analogous wires of a contiguous PSPMT.

3. The flat scintillation gamma camera according to claim 1, wherein said multiple square-shaped PSPMTs constitute an area of detection with a polygonal profile.

4. The flat scintillation gamma camera according to claim 1, comprising an operational amplifier (8) Performing hardware operations on input signals for the computation of a charge barycenter to take place via a weighted sum method, as represented by a formula for the barycenter.

5. The flat scintillation gamma camera according to claim 1, comprising an operational amplifier (8) performing hardware rations on the input signals having weighted resistance collection of charge in position of the dead zone, for computation of the charge barycenter taking place via a weighted sum method as represented by a formula for the barycenter.

6. The flat scintillation gamma camera according to claim 1, wherein each said PSPMT has a width (FWHM) at least as great as the interspace between contiguous PSPMT's and an anode sampling pitch.

7. The flat scintillation gamma camera according to claim 1, wherein each said PSPMT has a side not greater than 30 mm.

8. The flat scintillation gamma camera according to claim 7, wherein each said PSPMT has a side not greater than 22 mm.

9. The flat scintillation gamma camera according to claim 8, wherein each said PSPMT has a thickness not greater than 50 mm.

10. The flat scintillation gamma camera according to claim 7, wherein each said PSPMT has a thickness not greater than 50 mm.

* * * * *